(12) United States Patent
Childress et al.

(10) Patent No.: US 9,623,133 B2
(45) Date of Patent: Apr. 18, 2017

(54) LAVATORY DISINFECTION SYSTEM

(71) Applicant: The Boeing Company, Chicago, IL (US)

(72) Inventors: James J. Childress, Mercer Island, WA (US); Mark L. Cloud, Seattle, WA (US); Karen Lee Hills, Everett, WA (US)

(73) Assignee: THE BOEING COMPANY, Chicago, IL (US)

( * ) Notice: Subject to any disclaimer, the term of this patent is extended or adjusted under 35 U.S.C. 154(b) by 149 days.

(21) Appl. No.: 14/610,022

(22) Filed: Jan. 30, 2015

(65) Prior Publication Data
US 2016/0220716 A1    Aug. 4, 2016

(51) Int. Cl.
| | | |
|---|---|---|
| *A61L 2/00* | (2006.01) | |
| *A61N 5/00* | (2006.01) | |
| *G01N 23/00* | (2006.01) | |
| *A61L 2/24* | (2006.01) | |
| *A61L 2/10* | (2006.01) | |
| *H05B 37/02* | (2006.01) | |

(52) U.S. Cl.
CPC ........ *A61L 2/24* (2013.01); *A61L 2/10* (2013.01); *H05B 37/0227* (2013.01); *H05B 37/0281* (2013.01)

(58) Field of Classification Search
CPC ................ A61L 2/00; A61L 9/18; A61L 9/20
USPC .................. 422/1, 22–24; 250/455.11, 492.1
See application file for complete search history.

(56) References Cited

U.S. PATENT DOCUMENTS

| | | |
|---|---|---|
| 4,819,276 A | 4/1989 | Stevens |
| 5,364,645 A | 11/1994 | Lagunas-Solar et al. |
| 5,777,437 A | 7/1998 | Neister |
| 5,903,450 A | 5/1999 | Johnson et al. |
| 8,481,985 B2 | 7/2013 | Neister |
| 8,753,575 B2 | 6/2014 | Neister |
| 8,975,605 B2 | 3/2015 | Neister |
| 2013/0205487 A1* | 8/2013 | Yagi .................. E03D 11/13 4/420 |
| 2014/0059796 A1 | 3/2014 | Boodaghians et al. |
| 2014/0115764 A1 | 5/2014 | Cheng et al. |

FOREIGN PATENT DOCUMENTS

| | | |
|---|---|---|
| WO | WO2010087831 A1 | 8/2010 |
| WO | WO2010087831 A8 | 10/2011 |
| WO | WO2014036217 A2 | 3/2014 |

* cited by examiner

*Primary Examiner* — Monzer R Chorbaji
(74) *Attorney, Agent, or Firm* — Yee & Associates, P.C.

(57) ABSTRACT

A method and apparatus for disinfecting a lavatory inside a vehicle in response to a set of criteria being met. A determination is made as to whether a set of criteria for activation of a disinfection system that emits far-ultraviolet radiation to perform a disinfection process inside a lavatory has been met. In response to a determination that the set of criteria has been met, the disinfection system is activated to perform the disinfection process inside the lavatory using the far-ultraviolet radiation.

26 Claims, 7 Drawing Sheets

LAVATORY DISINFECTION SYSTEM

BACKGROUND INFORMATION

1. Field

The present disclosure relates generally to disinfection and, in particular, to disinfection of lavatories. Still more particularly, the present disclosure relates to a method and apparatus for disinfecting lavatories on vehicles using far-ultraviolet radiation.

2. Background

Pathogens may be spread between humans, between animals, or between humans and animals in many different ways. Consequently, there is an increasing need for the disinfection or sterilization of public areas and public spaces, particularly enclosed areas and spaces. As one example, a single aircraft may fly to multiple destinations on the same day. These destinations may include, for example, different airports, airstrips, or airfields in the same state, in different states, or in different countries. Any number of passengers and crewmembers may get on and off this single aircraft between flights. Further, the passengers and crewmembers onboard the aircraft during a single flight may be a diverse group coming from different backgrounds and environments. These conditions create the potential for the spread of pathogens onboard an aircraft.

One possible source for the spread of pathogens onboard an aircraft is inside the lavatory of the aircraft. Currently, the lavatories inside aircraft are cleaned manually. For example, one or more crewmembers or service personnel may clean the lavatories inside an aircraft between flights. Typically, disinfectant sprays, aerosols, or other types of cleaning solutions are used to disinfect surfaces. However, some of these materials may result in an undesired coating of material being left on the surfaces. The time required to dissipate certain types of aerosols or sprays may be longer than desired. Further, certain types of disinfectant materials may have odors that may be undesirable to some people.

Additionally, this type of manual disinfection of these lavatories may be more time-consuming than desired, may not be as effective as desired, or both. In some situations, performing this type of manual disinfection during flight may not be desirable or even feasible. Therefore, there may be a need for a method and apparatus that take into account at least some of the issues discussed above, as well as other possible issues.

SUMMARY

In one illustrative embodiment, an apparatus comprises a disinfection system and an activation system. The disinfection system emits far-ultraviolet radiation to perform a disinfection process inside a lavatory in a vehicle when the lavatory is not in use. The disinfection system is inactive when the lavatory is in use. The activation system controls activation and deactivation of the disinfection system.

In another illustrative embodiment, a method for disinfecting a lavatory is provided. A determination is made as to whether a set of criteria for activation of a disinfection system that emits far-ultraviolet radiation to perform a disinfection process inside a lavatory, has been met. In response to a determination that the set of criteria has been met, the disinfection system is activated, to perform the disinfection process inside the lavatory, using the far-ultraviolet radiation.

In yet another illustrative embodiment, a method for disinfecting a lavatory located inside an aerospace vehicle is provided. A determination is made as to whether the lavatory is unoccupied. In response to a determination that the lavatory is unoccupied, a determination is made as to whether the lavatory has been occupied a selected number of times since a previous disinfection of the lavatory. In response to a determination that the lavatory has been occupied the selected number of times since the previous disinfection of the lavatory, a determination is made as to whether a door to the lavatory is closed. In response to a determination that the door is closed, a disinfection system is activated to perform a disinfection process inside the lavatory using far-ultraviolet radiation. The disinfection system is deactivated after completion of the disinfection process.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. For example, the illustrative embodiments recognize and take into account that it may be desirable to have the capability of disinfecting the lavatories located in a vehicle, such as an aerospace vehicle. For example, it may be desirable to have the capability to disinfect a lavatory in an aerospace vehicle, such as an aircraft, during flight. Further, the illustrative embodiments recognize and take into account that it may be desirable to have a method and apparatus for disinfecting these lavatories to thereby reduce the need for a crewmember or some other type of person onboard the aircraft to perform the disinfection.

The illustrative embodiments recognize and take into account that ultraviolet radiation may be an effective form of disinfection. In particular, the illustrative embodiments recognize that far-ultraviolet (FUV) radiation may provide improved disinfection over other forms of ultraviolet radiation, such as, for example, without limitation, ultraviolet-C (UV-C) radiation. Far-ultraviolet radiation may be capable of destroying a greater number of pathogens and requires less exposure time for disinfection. Further, with respect to human exposure, far-ultraviolet radiation may be less harmful to humans as compared to ultraviolet-C radiation.

Thus, the illustrative embodiments provide a method and apparatus for disinfecting a lavatory using far-ultraviolet radiation. This disinfection may be performed in a manner that minimizes or prevents the exposure of humans to far-ultraviolet radiation. In one illustrative embodiment, an apparatus comprises a disinfection system and an activation system. The disinfection system emits far-ultraviolet radiation to perform a disinfection process inside a lavatory when the disinfection system is active. The disinfection system does not emit the far-ultraviolet radiation when inactive. The activation system controls activation and deactivation of the disinfection system.

Figure 1:
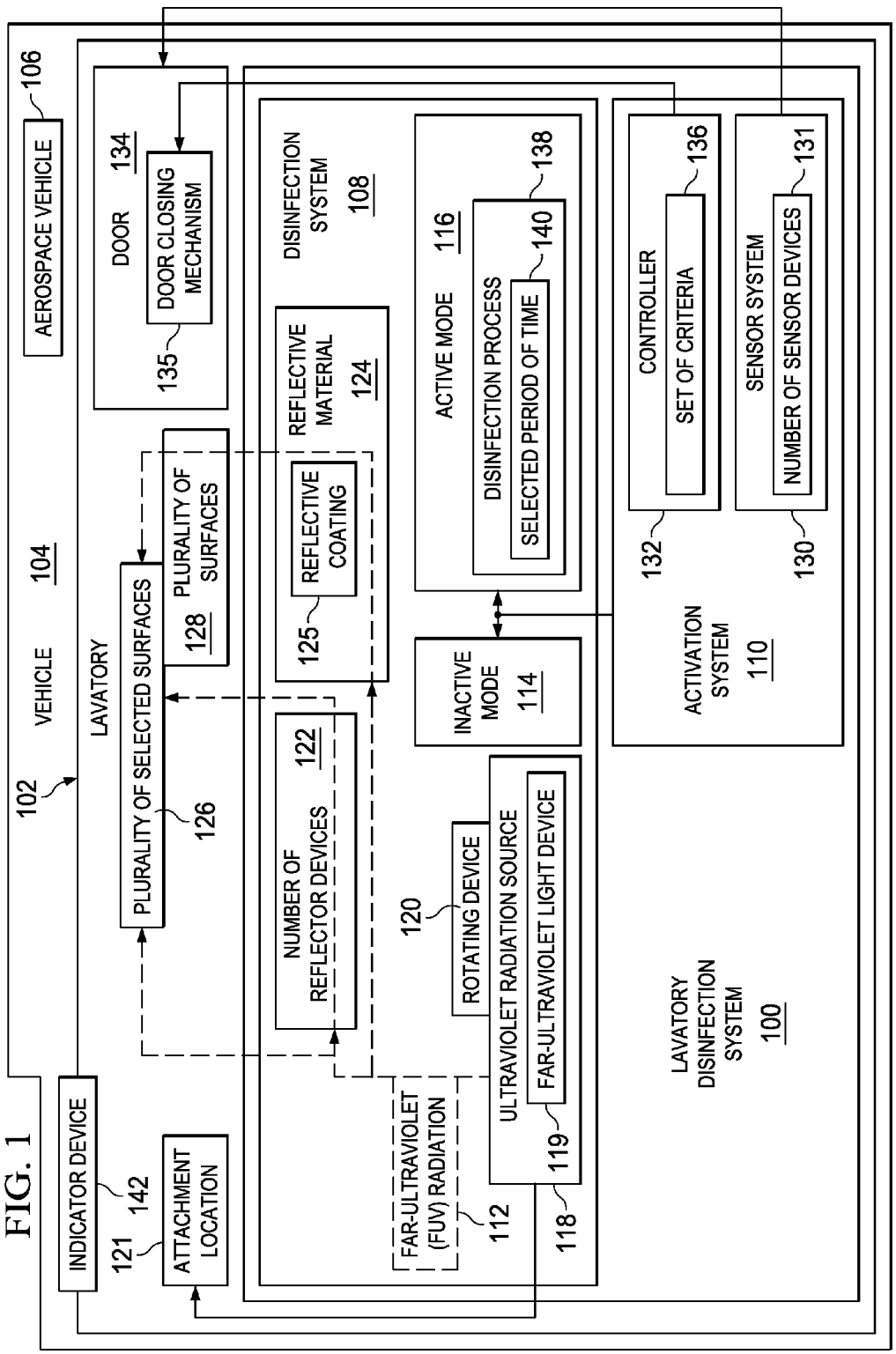
FIG. 1 is an illustration of a lavatory disinfection system in the form of a block diagram in accordance with an illustrative embodiment.

Referring now to the figures and, in particular, with reference to FIG. 1, an illustration of a lavatory disinfection system is depicted in the form of a block diagram in accordance with an illustrative embodiment. In this illustrative example, lavatory disinfection system 100 may be used to disinfect lavatory 102.

As depicted, lavatory 102 may be located in vehicle 104. Vehicle 104 may take the form of aerospace vehicle 106. Aerospace vehicle 106 may be selected from one of an aircraft, a spacecraft, a space shuttle, a space station, or some other type of aerospace vehicle. In other illustrative examples, vehicle 104 may take the form of a ground vehicle or a water vehicle, such as a ship.

Lavatory disinfection system 100 may include disinfection system 108 and activation system 110. Depending on the implementation, disinfection system 108 and activation system 110 may be considered separate systems working in conjunction with each other to form lavatory disinfection system 100 or two systems that are integrated with each other to form lavatory disinfection system 100.

Disinfection system 108 may use far-ultraviolet (FUV) radiation 112 to disinfect lavatory 102. Activation system 110 may control when disinfection system 108 is activated and when disinfection system 108 is deactivated. When activated, disinfection system 108 enters active mode 116 where disinfection system 108 emits far-ultraviolet radiation 112. When in inactive mode 114, no far-ultraviolet radiation 112 is emitted until the disinfection system 108 is reactivated. In some cases, inactive mode 114 may be referred to as a "standby" mode, because disinfection system 108 remains inactive and on a temporal "standby" until the activation or the reactivation of disinfection system 108.

In one illustrative example, disinfection system 108 includes ultraviolet radiation source 118. Ultraviolet radiation source 118 may take the form of, for example, without limitation, far-ultraviolet light device 119.

Ultraviolet radiation source 118 may be configured to emit far-ultraviolet radiation 112, which may also be referred to as far-ultraviolet light. Far-ultraviolet radiation 112 may have a wavelength between about 150 nanometers (nm) and 240 nanometers (nm). In one illustrative example, far-ultraviolet radiation 112 may be selected as having a wavelength of about 222 nanometers.

Ultraviolet radiation source 118 may be mounted to any surface inside lavatory 102, a surface within a vent or other access opening that opens into lavatory 102, or some other type of surface. In particular, ultraviolet radiation source 118 may be mounted to a location that allows far-ultraviolet radiation 112 emitted by ultraviolet radiation source 118 to encounter the greatest number of surfaces inside lavatory 102. As one illustrative example, ultraviolet radiation source 118 may be mounted to attachment location 121 inside lavatory 102.

Attachment location 121 may be any location inside lavatory 102 or on any surface of lavatory 102. In one illustrative example, attachment location 121 may be selected such that far-ultraviolet radiation 112 emitted by ultraviolet radiation source 118 reaches the largest portion of the greatest number of surfaces in lavatory 102 that need to disinfected. For example, without limitation, attachment location 121 may be on a top surface or ceiling of lavatory 102 or on a top portion of a side surface of lavatory 102. As another example, attachment location 121 may be on the interior-facing side of door 134 that opens to lavatory 102.

In some illustrative examples, ultraviolet radiation source 118 may emit far-ultraviolet radiation 112 in the form of one or more beams. These one or more beams may be focused beams. In some cases, ultraviolet radiation source 118 may be mounted to rotating device 120. Rotating device 120 may be used to rotate ultraviolet radiation source 118 to rotate the one or more beams of far-ultraviolet radiation 112 such that far-ultraviolet radiation 112 becomes incident on more than one surface.

As depicted, disinfection system 108 may also include number of reflector devices 122. As used herein, a "number of" items may include one or more items. In this manner, number of reflector devices 122 may include one or more reflector devices 122. Each of number of reflector devices 122 may be positioned inside lavatory 102 such that far-ultraviolet radiation 112 that encounters the reflector device may be reflected. In particular, number of reflector devices 122 may be positioned such that far-ultraviolet radiation 112 is reflected onto at least one selected surface inside lavatory 102.

In some illustrative examples, disinfection system 108 may also include reflective material 124. In one illustrative example, reflective material 124 may take the form of reflective coating 125 applied to plurality of surfaces 128 inside lavatory 102 to reflect far-ultraviolet radiation 112 onto at least one selected surface inside lavatory 102. In other illustrative examples, reflective material 124 may be part of the surface material of each of plurality of surfaces 128.

Reflective material 124 may selectively reflect far-ultraviolet radiation 112, but not electromagnetic radiation of human eye optical wavelengths. Consequently, reflective material 124 may be inconspicuous to the human user. For example, a human user of lavatory 102 may be unaware that reflective material 124 is present. In other words, reflective material 124 may not be noticeable to humans.

In this manner, far-ultraviolet radiation 112 emitted by ultraviolet radiation source 118 and far-ultraviolet radiation 112 reflected by number of reflector devices 122, reflective material 124, or both may be directed towards and encounter plurality of selected surfaces 126. Once far-ultraviolet radiation 112 encounters plurality of selected surfaces 126, far-ultraviolet radiation 112 begins disinfecting plurality of selected surfaces 126. Disinfecting plurality of selected surfaces 126 comprises destroying potential pathogens that may be present on plurality of selected surfaces 126.

Plurality of selected surfaces 126 may include any surfaces inside lavatory 102 that may need to be disinfected due to the potential for contact with at least one of a person, animal, or object carrying any number of pathogens. Plurality of selected surfaces 126 may include, for example, without limitation, surfaces on and around a toilet inside lavatory 102, surfaces inside and around a sink inside lavatory 102, a floor of lavatory 102, one or more door handles, one or more drawer handles or cabinet knobs, other types of surfaces that can become infected through contact with at least one of a person, animal, object, or some combination thereof.

Activation system 110 may control whether disinfection system 108 is in active mode 116 or in inactive mode 114. Active mode 116 may also be referred to as a disinfecting mode or an operational mode, in some cases. Activation system 110 may include sensor system 130 and controller 132. Sensor system 130 may be used to detect when lavatory 102 is occupied or unoccupied and when door 134 to lavatory 102 is closed or open.

Sensor system 130 may include number of sensor devices 131 for monitoring the occupancy of lavatory 102 and whether or not door 134 is open or closed. Number of sensor devices 131 may include any number of different types of sensor types that are configured to detect and signal when the lavatory is occupied or empty. For example, without limitation, number of sensor devices 131 may include at least one of a motion sensor, an occupancy sensor, a thermal sensor, an open/close sensor, an infrared sensor device, an ultrasonic sensor device, a floor pressure sensor, or some other type of sensor.

As used herein, the phrase "at least one of," when used with a list of items, means different combinations of one or more of the listed items may be used or only one of the items in the list may be used. The item may be a particular object, thing, or category. In other words, "at least one of" means any combination of items or number of items may be used from the list, but not all of the items in the list may be required.

For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Sensor system 130 may monitor the occupancy of lavatory 102 and the status of door 134 with respect to being open or closed and generate information based on this monitoring. This information may take the form of, for example, without limitation, at least one of an electrical signal, a radio signal, an optical signal, some other type of wired signal, some other type of wireless signal, or some other type of signal. Sensor system 130 may send this information indicating whether or not lavatory 102 is occupied, and whether or not door 134 is open, to controller 132.

Controller 132 may be implemented using hardware, firmware, software, or some combination thereof. Controller 132 may use the information received from sensor system 130 to determine whether set of criteria 136 has been met. In this illustrative example, set of criteria 136 may include lavatory 102 being unoccupied, door 134 to lavatory 102 being closed, lavatory 102 having been occupied a selected number of times since a previous disinfection of lavatory 102, a selected amount of time having passed since a previous disinfection of lavatory 102, a selected amount of time having passed since some reference point in time or event, some other type of criteria, or some combination thereof.

The selected number of times that lavatory 102 may need to be occupied since a previous disinfection of lavatory 102 may be, for example, without limitation, one time, two times, three times, or some other number of times. In some cases, no occupants may enter lavatory 102 after a previous disinfection. Consequently, in some cases, the selected number of times that lavatory 102 may need to be occupied since a previous disinfection of lavatory 102 may be set to zero times.

The selected amount of time that may need to pass since the previous disinfection of lavatory 102 may be, for example, without limitation, five minutes, ten minutes, thirty minutes, one hour, two hours, five hours, twenty-four hours, or some other period of time. When lavatory disinfection system 100 is being used for the first time, there may be no previous disinfection to consider. Consequently, the selected amount of time may be with respect to some other reference point in time.

In one illustrative example, set of criteria 136 may include a threshold level of pathogen presence, a threshold level of impurity presence, or both, within lavatory 102. For example, without limitation, sensor system 130 may include at least one of an air sampling device, an air quality sensor, a pathogen detection system, or some other type of sensor device capable of detecting the level of pathogens, impurities, or both present in lavatory 102. Pathogens may include pathogens on a surface, airborne pathogens, or both. Impurities may include, for example, inanimate contaminants on a surface, airborne inanimate contaminants, or both. This type of criterion may be met when the threshold level of pathogen presence, threshold level of impurity presence, or both has been met.

In these illustrative examples, set of criteria 136 may at least include that lavatory 102 be unoccupied such that disinfection system 108 is never in active mode 116 when lavatory 102 is occupied, for safety reasons. In response to controller 132 determining that set of criteria 136 has been met, controller 132 activates disinfection system 108, thereby placing disinfection system 108 in active mode 116. Upon entering active mode 116, disinfection system 108 may begin performing disinfection process 138 to disinfect plurality of selected surfaces 126. In some cases, far-ultraviolet radiation 112 may also be capable of disinfecting the air inside lavatory 102 by at least one of destroying or neutralizing pathogens, impurities, or both.

In some illustrative examples, door closing mechanism 135 may be associated with door 134. When controller 132 determines that lavatory 102 is unoccupied and that all criteria in set of criteria 136 have been met except for door 134 being closed, controller 132 may engage door closing mechanism 135. Door closing mechanism 135 closes door 134 automatically, such that the criterion of door 134 to lavatory 102 being closed, can then be met.

Disinfection process 138 may include, for example, without limitation, emitting far-ultraviolet radiation 112 from ultraviolet radiation source 118 for selected period of time 140. In some cases, disinfection process 138 may include rotating ultraviolet radiation source 118 continuously or periodically during selected period of time 140.

Exposure of plurality of selected surfaces 126 to far-ultraviolet radiation 112 for a short period of time may destroy, for example, without limitation, greater than about 95 percent or more of the pathogens present on plurality of selected surfaces 126. Selected period of time 140 may be selected based on the minimum amount of time needed to fully disinfect lavatory 102 within selected tolerances. The minimum amount of time needed to disinfect within selected tolerances may be a function of, for example, without limitation, the energy of far-ultraviolet radiation 112 incident per square centimeter.

As one illustrative example, selected period of time 140 may be the minimum amount of time needed to fully disinfect plurality of selected surfaces 126 such that greater than about 99 percent of the undesired pathogens inside lavatory 102 are destroyed. Selected period of time 140 may be selected as, for example, without limitation, about 3, 5, 8, 10, 15, 20, 30, or some other number of seconds.

Once disinfection process 138 has been completed, controller 132 deactivates disinfection system 108, thereby placing disinfection system 108 in inactive mode 114. In some cases, door 134 to lavatory 102 may be opened during disinfection process 138. If sensor system 130 detects the opening of door 134 during disinfection process 138, then controller 132 deactivates disinfection system 108 to place disinfection system 108 in inactive mode 114.

By using ultraviolet radiation source 118 that emits far-ultraviolet radiation 112, the emission of far-ultraviolet radiation 112 from ultraviolet radiation source 118 may be halted substantially immediately upon deactivation of disinfection system 108. For example, when disinfection system 108 is deactivated, ultraviolet radiation source 118 may be turned off such that the emission of far-ultraviolet radiation 112 is halted within less than a second.

Depending on the configuration of ultraviolet radiation source 118, the emission of far-ultraviolet radiation 112 may be halted within milliseconds or microseconds. Using an electric arc-based source as ultraviolet radiation source 118 may enable the halting of the emission of far-ultraviolet radiation 112 within milliseconds or microseconds.

For example, ultraviolet radiation source 118 may be equipped with a controller switch that halts power supply to far-ultraviolet radiation source 118 within a desired, relatively short time following the opening of door 134 to lavatory 102. In this manner, the safety of any person or animal that opens door 134 to lavatory 102 during disinfection process 138 may be ensured.

In some illustrative examples, indicator device 142 may be associated with an exterior of lavatory 102. Indicator device 142 may display a visual indication of whether disinfection system 108 is in active mode 116 or in inactive mode 114. As one illustrative example, indicator device 142 may be a digital display. In some cases, indicator device 142 or some other type of indicator device may be used to visually indicate when disinfection process 138 has been completed and lavatory 102 is ready for use.

In this manner, lavatory disinfection system 100 provides an effective and fast system for disinfecting lavatory 102. Using far-ultraviolet radiation 112, which has a shorter wavelength and higher frequency than other types of ultraviolet radiation, such as ultraviolet-C radiation, may be more effective than using lower-frequency, longer-wavelength ultraviolet radiation. Far-ultraviolet radiation 112 may be used to at least one of destroy or neutralize pathogens, impurities, or both. Pathogens may include bacteria, viruses, other types of microorganisms, or some combination thereof. A short-time exposure to far-ultraviolet radiation 112 may destroy a desired percentage of pathogens. For example, far-ultraviolet radiation 112 may enable destruction of substantially all contaminants present. Further, using far-ultraviolet radiation 112 as compared to other types of longer-wavelength ultraviolet radiation may reduce the amount of power required for lavatory disinfection system 100.

Although the activation of disinfection system 108 is described above as being automated by activation system 110 based on set of criteria 136 being met, in some illustrative examples, disinfection system 108 may be capable of being manually activated. For example, without limitation, disinfection system 108 may have an additional manual activation switch device that may be operable by, for example, a human when the lavatory is unoccupied or vacant.

In other illustrative examples, lavatory disinfection system 100 may include one or more mechanical systems capable of physically moving one or more components inside lavatory 102 during disinfection process 138 to expose additional surfaces for disinfection. As one illustrative example, a mechanism may be associated with a toilet inside lavatory 102. This mechanism may be used to lift a lid of the toilet to enable exposure of the toilet seat to far-ultraviolet radiation 112 during disinfection process 138. In some cases, the mechanism may be used to lift the toilet seat of the toilet to enable exposure of other toilet surfaces to far-ultraviolet radiation 112 during disinfection process 138.

Operation of these types of mechanisms may be triggered once disinfection process 138 begins. For example, these mechanisms may be triggered to operate after the lapse of a timer after disinfection process 138 begins or immediately after disinfection process 138 begins.

Lavatory disinfection system 100 may be implemented in such a manner that enables lavatory disinfection system 100 to be retrofitted in aerospace vehicle 106. Using this type of system that can be either installed in lavatory 102 of aerospace vehicle 106 during manufacturing or retrofitted to aerospace vehicle 106 during maintenance, service, or repair may help reduce the overall costs associated with this type of disinfection system.

The illustration of lavatory disinfection system 100 in FIG. 1 is not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

In other illustrative examples, lavatory disinfection system 100 may not include door closing mechanism 135. In some illustrative examples, more than one door may provide access to lavatory 102. Set of criteria 136 may include that all of the doors that provide access to lavatory 102 be closed. In still other illustrative examples, number of reflector devices 122 may be excluded and only reflective material 124 used to ensure that each of plurality of surfaces 128 will be reached by far-ultraviolet radiation 112.

In some cases, lavatory disinfection system 100 may be used to disinfect a lavatory or restroom inside a building, a restaurant, a store, a mall, an office building, or some other type of structure. Further, although disinfection system 108 and activation system 110 have been described for use in disinfecting lavatory 102 inside aerospace vehicle 106, at least one of disinfection system 108 or activation system 110 may be used for the disinfection of other areas inside aerospace vehicle 106.

As one illustrative example, multiple disinfection systems implemented in a manner similar to disinfection system 108 may be positioned throughout aerospace vehicle 106. For example, one or more disinfection systems may be positioned within at least one of a cabin area of aerospace vehicle 106, a galley area of aerospace vehicle 106, an interior of a duct or vent in aerospace vehicle 106, or in some other area of aerospace vehicle 106. Controller 132 or some other type of controller may be used to activate these disinfection systems between flights of aerospace vehicle 106 or during other times when there is no risk of humans or animals being exposed to far-ultraviolet radiation.

In still other illustrative examples, a system comprised of any number of disinfection systems implemented in a manner similar to disinfection system 108 and any number of activation systems implemented in a manner similar to activation system 110 may be used to disinfect other types of public areas. For example, this type of system may be used in airport baggage areas, airport waiting areas, airport gates, airport restrooms, airport restaurants, or some combination thereof.

Figure 2:
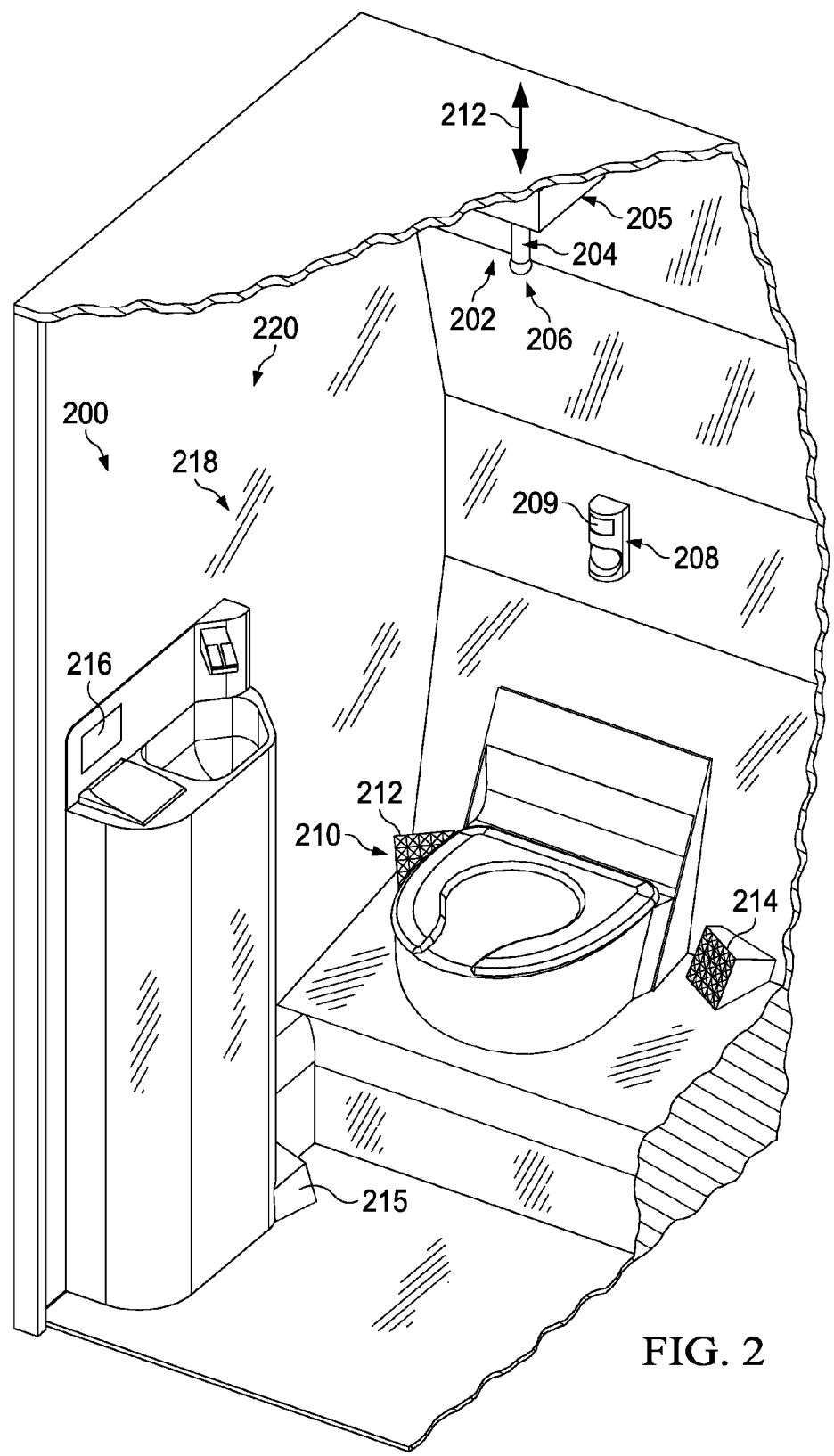
FIG. 2 is an illustration of an isometric view of a lavatory of an aircraft in accordance with an illustrative embodiment.

With reference now to FIG. 2, an illustration of an isometric view of a lavatory of an aircraft is depicted in accordance with an illustrative embodiment. In this illustrative example, lavatory 200 may be an example of one implementation for lavatory 102 in FIG. 1. As depicted, lavatory disinfection system 202 is present inside lavatory 200. Lavatory disinfection system 202 is an example of one implementation for lavatory disinfection system 100 in FIG. 1.

Lavatory disinfection system 202 includes disinfection system 204 and activation system 205, which may be examples of implementations for disinfection system 108 and activation system 110, respectively, in FIG. 1. Activation system 205 includes sensor system 208, which may be an example of one implementation for sensor system 130 in FIG. 1. Sensor system 208 may include occupancy sensor 209 and an open/close sensor (not shown).

Disinfection system 204 includes far-ultraviolet light device 206, which may be an example of one implementation for far-ultraviolet light device 119 in FIG. 1, and thereby, ultraviolet radiation source 118 in FIG. 1. Disinfection system 204 also includes number of reflector devices 210 and reflective material 218. Number of reflector devices 210 may be an example of one implementation for number of reflector devices 122 in FIG. 1. Reflective material 218 may be an example of one implementation for reflective material 124 in FIG. 1.

Number of reflector devices 210 may include reflector device 212, reflector device 214, reflector device 215, and reflector device 216. As depicted, reflective material 218 may be applied to plurality of surfaces 220 inside lavatory 200.

When disinfection system 204 is in an active mode, far-ultraviolet light device 206 emits far-ultraviolet radiation. This far-ultraviolet radiation may be emitted towards various surfaces inside lavatory 200. The portion of far-ultraviolet radiation that encounters reflective material 218 and each of number of reflector devices 210 may be reflected. In particular, each of number of reflector devices 210 may be positioned to cause the reflection of far-ultraviolet radiation onto one or more selected surfaces inside lavatory 102. In this manner, disinfection system 204 may be configured such that far-ultraviolet radiation reaches a plurality of selected surfaces inside lavatory 200 that need to be disinfected.

Figure 3:
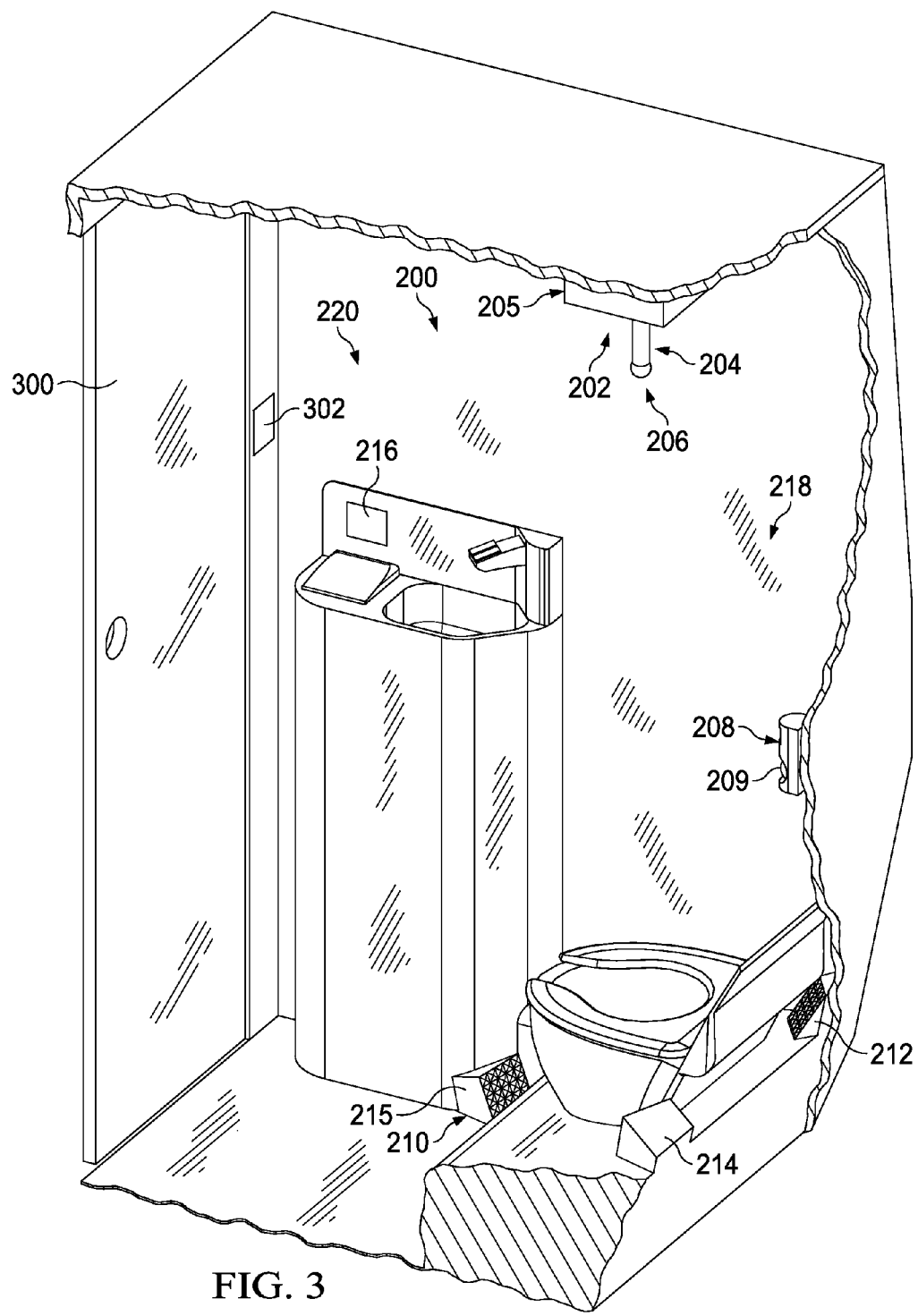
FIG. 3 is an illustration of another view of a lavatory in accordance with an illustrative embodiment.

With reference now to FIG. 3, an illustration of another view of lavatory 200 from FIG. 2 is depicted in accordance with an illustrative embodiment. In this illustrative example, door 300 to lavatory 200 may be seen. Open/close sensor 302 is associated with door 300. Open/close sensor 302 is configured to detect when door 300 is open and when door 300 is closed.

Activation system 205 may use the information provided by sensor system 208 to determine when to place disinfection system 204 in an active mode and when to place disinfection system 204 in an inactive mode. Disinfection system 204 is only activated when door 300 to lavatory 200 is closed, when lavatory 200 is unoccupied, and when lavatory 200 has been occupied a selected number of times since a previous disinfection of lavatory 200.

In addition, disinfection system 204 may be activated when a selected amount of time has passed since a previous disinfection of lavatory 200, provided lavatory 200 is unoccupied. If lavatory 200 is occupied at the lapse of the selected amount of time since the previous disinfection, a controller, such as controller 132, of disinfection system 204 may have an override capability to ensure that disinfection system 204 does not activate when lavatory 200 is occupied.

Figure 4:
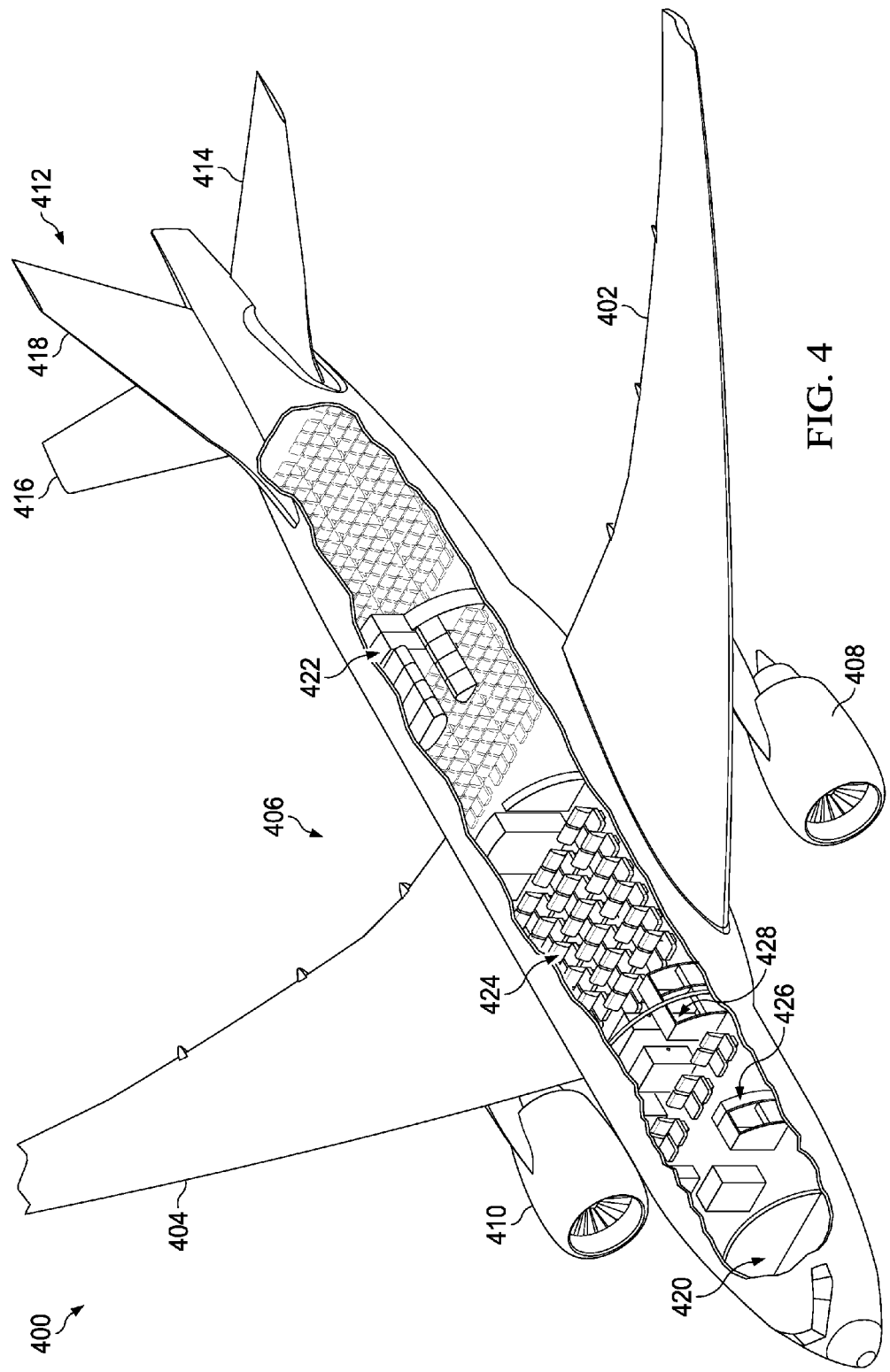
FIG. 4 is an illustration of an isometric cut-away view of an aircraft in accordance with an illustrative embodiment.

With reference now to FIG. 4, an illustration of an isometric cut-away view of an aircraft is depicted in accordance with an illustrative embodiment. Aircraft 400 may be an example of one implementation for aerospace vehicle 106 in FIG. 1.

In this illustrative example, aircraft 400 has wing 402 and wing 404 attached to body 406. Body 406 may also be referred to as a fuselage. Aircraft 400 includes engine 408 attached to wing 402 and engine 410 attached to wing 404. Body 406 has tail section 412. Horizontal stabilizer 414, horizontal stabilizer 416, and vertical stabilizer 418 are attached to tail section 412 of body 406.

Body 406 also has cockpit 420 and passenger cabin 422. In this example, passenger cabin 422 may include passenger seating in seating area 424. Further, seating area 424 in passenger cabin 422 may include storage areas, such as a number of overhead stowage bins. Passenger cabin 422 may include lavatory 426 and galley area 428.

Lavatory 426 may be another example of an implementation for lavatory 102 in FIG. 1. In this illustrative example, lavatory 426 may be implemented in a manner similar to lavatory 200 in FIGS. 2-3. Further, a lavatory disinfection system, such as lavatory disinfection system 202 in FIGS. 2-3, may be installed in lavatory 426.

In some illustrative examples, a system comprised of one or more disinfection systems implemented similarly to disinfection system 108 described in FIG. 1 and one or more activation systems implemented similarly to activation system 110 in FIG. 1 may be installed in aircraft 400 such that multiple areas throughout aircraft 400 may be disinfected. For example, this type of system may be used to disinfect galley area 428, cockpit 420, seating area 424 within passenger cabin 422, the interior surfaces of storage areas within passenger cabin 422, other areas inside passenger cabin 422, other areas inside aircraft 400, or some combination thereof.

The illustrations of lavatory 200 in FIGS. 2-3 and aircraft 400 in FIG. 4 are provided for purposes of illustrating one environment in which the different illustrative embodiments may be implemented. The illustrations in FIGS. 2-4 are not meant to imply physical or architectural limitations as to the manner in which different illustrative embodiments may be implemented.

The different components shown in FIGS. 2-4 may be illustrative examples of how components shown in block form in FIG. 1 can be implemented as physical structures. Additionally, some of the components in FIGS. 2-4 may be combined with components in FIG. 1, used with components in FIG. 1, or a combination of the two.

Figure 5:
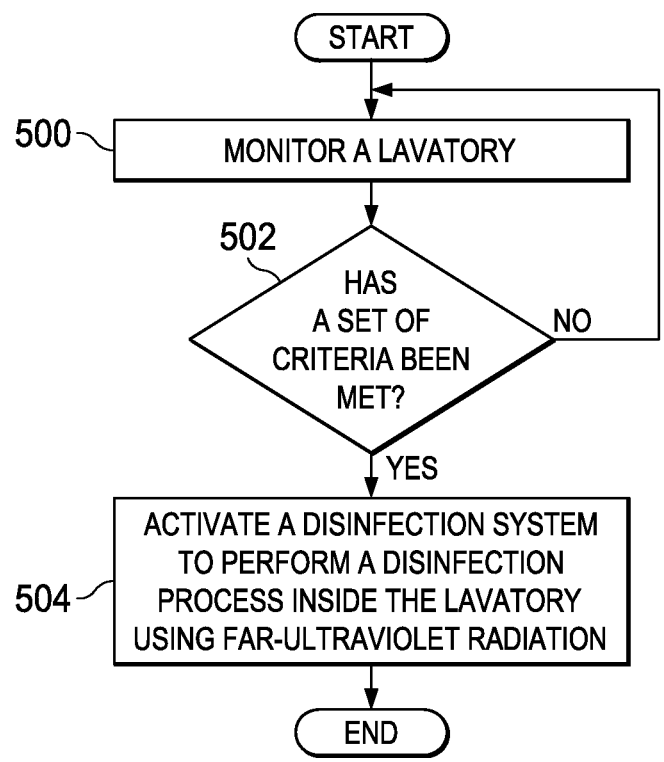
FIG. 5 is an illustration of a process for disinfecting a lavatory in the form of a flowchart in accordance with an illustrative embodiment.

With reference now to FIG. 5, an illustration of a process for disinfecting a lavatory is depicted in the form of a flowchart in accordance with an illustrative embodiment. The process illustrated in FIG. 5 may be implemented using, for example, lavatory disinfection system 100 in FIG. 1.

The process may begin by monitoring a lavatory (operation 500). In one illustrative example, operation 500 may be performed by monitoring occupancy of the lavatory and a door to the lavatory. The occupancy of the lavatory and the door the lavatory may be monitored in operation 500 using, for example, without limitation, a sensor system.

A determination may be made as to whether a set of criteria has been met (operation 502). The set of criteria may include the lavatory being unoccupied and at least one of, for example, without limitation, the door to the lavatory being closed, the lavatory having been occupied a selected number of times since a previous disinfection of the lavatory, or a selected amount of time having passed since the previous disinfection of the lavatory. The selected number of times that the lavatory must be occupied since a previous disinfection of the lavatory may be, for example, without limitation, one time, two times, three times, or some other number of times. The selected amount of time that needs to pass since the previous disinfection of the lavatory may be, for example, without limitation, five minutes, ten minutes, thirty minutes, one hour, two hours, five hours, twenty-four hours, or some other period of time.

If the set of criteria has not been met, the process returns to operation 500 as described above. Otherwise, if the set of criteria has been met, a disinfection system is activated to perform a disinfection process inside the lavatory using far-ultraviolet radiation (operation 504), with the process terminating thereafter. In this illustrative example, in operation 504, the disinfection process may include emitting far-ultraviolet radiation for a selected period of time. For example, far-ultraviolet radiation may be emitted for about five seconds, ten seconds, or some other period of time.

Figure 6:
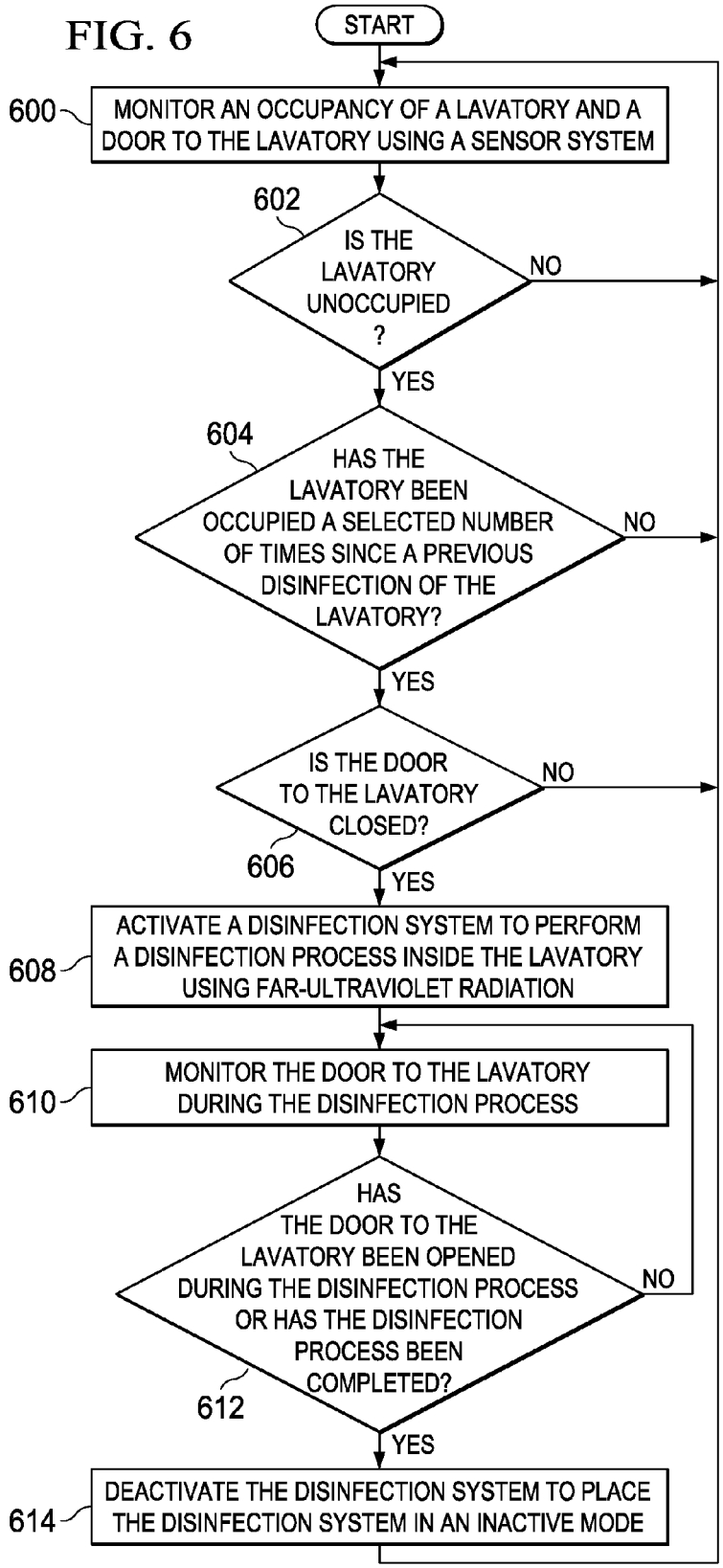
FIG. 6 is an illustration of a process for disinfecting a lavatory located in an aerospace vehicle in the form of a flowchart in accordance with an illustrative embodiment.

With reference now to FIG. 6, an illustration of a process for disinfecting a lavatory located in an aerospace vehicle is depicted in the form of a flowchart in accordance with an illustrative embodiment. The process illustrated in FIG. 6 may be implemented using, for example, lavatory disinfection system 100 in FIG. 1.

The process may begin by monitoring an occupancy of a lavatory and a door to the lavatory using a sensor system (operation 600). A determination may be made as to whether the lavatory is unoccupied (operation 602). If the lavatory is not unoccupied or, in other words, occupied, the process returns to operation 600 as described above. Otherwise, if the lavatory is unoccupied, a determination may be made as to whether the lavatory has been occupied a selected number of times since a previous disinfection of the lavatory (operation 604).

In operation 604, the previous disinfection is the most recent performance of a fully completed disinfection process. In some illustrative examples, operation 604 may include determining whether a selected amount of time has passed since a previous disinfection of the lavatory in addition to or in place of the determination as to whether the lavatory has been occupied a selected number of times since a previous disinfection of the lavatory.

If the lavatory has not been occupied the selected number of times since the previous disinfection of the lavatory, the process returns to operation 600 as described above. Otherwise, a determination may be made as to whether the door to the lavatory is closed (operation 606).

In one illustrative example, the door to the lavatory may be considered closed when the door is fully closed. If the door to the lavatory is not closed, the process returns to operation 600 as described above. Otherwise, if the door to the lavatory is closed, a disinfection system is activated to perform a disinfection process inside the lavatory using far-ultraviolet radiation (operation 608). In operation 608, activation of the disinfection system places the disinfection system in an active mode.

The door to the lavatory may be monitored during the disinfection process (operation 610). A determination may be made as to whether the door to the lavatory has been opened during the disinfection process or the disinfection process has been completed (operation 612). In operation 612, the door may be considered open even if the door is only partially opened.

If either the door to the lavatory has been opened during the disinfection process or the disinfection process has been completed, the disinfection system is deactivated to place the disinfection system in an inactive mode (operation 614), with the process then returning to operation 600 as described above. However, if the door has not been opened and the disinfection process has not been completed, the process returns to operation 610 as described above.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, in some cases, a determination that the door to the lavatory is not closed in operation 606 in FIG. 6 may cause a door closing mechanism to be automatically engaged instead of the process returning to operation 600. Once engaged, the door closing mechanism may close the door to the lavatory and the process may then proceed to operation 608.

Figure 7:
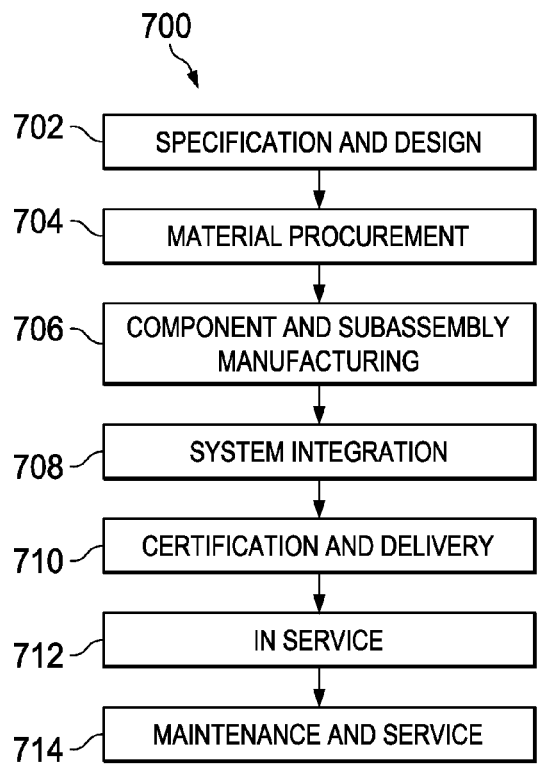
FIG. 7 is an illustration of an aircraft manufacturing and service method in the form of a block diagram in accordance with an illustrative embodiment.
Figure 8:
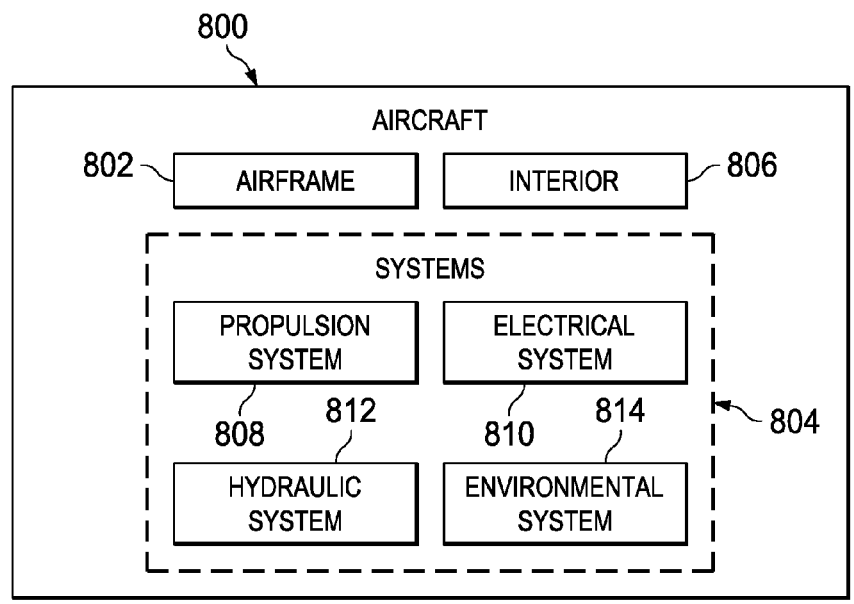
FIG. 8 is an illustration of an aircraft in the form of a block diagram in which an illustrative embodiment may be implemented.

The illustrative embodiments of the disclosure may be described in the context of aircraft manufacturing and service method 700 as shown in FIG. 7 and aircraft 800 as shown in FIG. 8. Turning first to FIG. 7, an illustration of an aircraft manufacturing and service method is depicted in the form of a block diagram in accordance with an illustrative embodiment. During pre-production, aircraft manufacturing and service method 700 may include specification and design 702 of aircraft 800 in FIG. 8 and material procurement 704.

During production, component and subassembly manufacturing 706 and system integration 708 of aircraft 800 in FIG. 8 takes place. Thereafter, aircraft 800 in FIG. 8 may go through certification and delivery 710 in order to be placed in service 712. While in service 712 by a customer, aircraft 800 in FIG. 8 is scheduled for routine maintenance and service 714, which may include modification, reconfiguration, refurbishment, and other maintenance or service.

Each of the processes of aircraft manufacturing and service method 700 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 8, an illustration of an aircraft is depicted in the form of a block diagram in which an illustrative embodiment may be implemented. In this example, aircraft 800 is produced by aircraft manufacturing and service method 700 in FIG. 7 and may include airframe 802 with plurality of systems 804 and interior 806. Examples of systems 804 include one or more of propulsion system 808, electrical system 810, hydraulic system 812, and environmental system 814. Any number of other systems may be included. Although an aerospace example is shown, different illustrative embodiments may be applied to other industries, such as the automotive industry.

The apparatuses and methods embodied herein may be employed during at least one of the stages of aircraft manufacturing and service method 700 in FIG. 7. In particular, lavatory disinfection system 100 from FIG. 1 may be installed on aircraft 800 during any one of the stages of aircraft manufacturing and service method 700. For example, without limitation, lavatory disinfection system 100 from FIG. 1 may be installed on aircraft 800 during at least one of component and subassembly manufacturing 706, system integration 708, routine maintenance and service 714, or some other stage of aircraft manufacturing and service method 700. Still further, lavatory disinfection system 100 from FIG. 1 may be used while aircraft 800 is in service 712 in FIG. 7.

In one illustrative example, components or subassemblies produced in component and subassembly manufacturing 706 in FIG. 7 may be fabricated or manufactured in a manner similar to components or subassemblies produced while aircraft 800 is in service 712 in FIG. 7. As yet another example, one or more apparatus embodiments, method embodiments, or a combination thereof may be utilized during production stages, such as component and subassembly manufacturing 706 and system integration 708 in FIG. 7. One or more apparatus embodiments, method embodiments, or a combination thereof may be utilized while aircraft 800 is in service 712 and/or during maintenance and service 714 in FIG. 7. The use of a number of the different illustrative embodiments may substantially expedite the assembly of and/or reduce the cost of aircraft 800.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a disinfection system to perform a disinfection process inside a lavatory when the lavatory is not in use, wherein the disinfection system is inactive when the lavatory is in use; and
an activation system that controls activation and deactivation of the disinfection system;
wherein the disinfection system comprises a source of far ultraviolet radiation, the source located in or on a ceiling of the lavatory to perform the disinfection process on at least one surface inside the lavatory.

2. The apparatus of claim 1, wherein the activation system activates the disinfection system in response to a determination that a set of criteria has been met, wherein the set of criteria includes the lavatory being unoccupied and at least one of a door to the lavatory being closed, the lavatory having been occupied a selected number of times since a previous disinfection of the lavatory, or a selected amount of time having passed since the previous disinfection of the lavatory.

3. The apparatus of claim 2, wherein the activation system comprises:
a sensor system that detects whether the lavatory is occupied or unoccupied and whether the door to the lavatory is closed or open.

4. The apparatus of claim 3, wherein the activation system further comprises:
a controller that receives information from the sensor system, determines whether the set of criteria has been met based on the information, and activates the disinfection system to place the disinfection system in an active mode in response to the determination that the set of criteria has been met.

5. The apparatus of claim 4, wherein the controller deactivates the disinfection system to place the disinfection system in an inactive mode when the door to the lavatory is opened prior to completion of the disinfection process.

6. The apparatus of claim 4, wherein the controller deactivates the disinfection system to place the disinfection system in an inactive mode after completion of the disinfection process.

7. The apparatus of claim 1 further comprising:
a reflective material applied to a plurality of surfaces inside the lavatory to reflect the far-ultraviolet radiation onto at least one selected surface inside the lavatory.

8. The apparatus of claim 1, wherein the disinfection system comprises:
an ultraviolet radiation source that emits the far-ultraviolet radiation, wherein the far-ultraviolet radiation has a wavelength between about 150 nanometers and about 240 nanometers.

9. The apparatus of claim 1, wherein the disinfection system further comprises:
a number of reflector devices that reflect the far-ultraviolet radiation onto at least one selected surface inside the lavatory.

10. The apparatus of claim 1 further comprising:
an indicator device associated with an exterior of the lavatory, wherein the indicator device displays a visual indication of whether the disinfection system is in an active mode or in an inactive mode.

11. An aircraft incorporating the apparatus of claim 1.

12. The apparatus of claim 1, further comprising:
a mechanism for lifting a lid of a toilet in the lavatory to expose the lid to the far-ultraviolet radiation, wherein, responsive to an activation of the disinfection system, the mechanism lifts the lid of the toilet to expose the lid to the far-ultraviolet radiation.

13. The apparatus of claim 1, further comprising:
a reflective material applied to a plurality of surfaces inside the lavatory to reflect the far-ultraviolet radiation onto one or more selected surfaces inside the lavatory;
wherein the source directs the far-ultraviolet radiation at the reflective material in order to disinfect the one or more selected surfaces.

14. The apparatus of claim 13, wherein the selected surfaces are a floor surface around a toilet of the lavatory, a drawer handle or a cabinet knob, and a sink surface in and around a sink in the lavatory.

15. The apparatus of claim 1, further comprising:
a number of reflective devices inside the lavatory to reflect the far-ultraviolet radiation onto an external surface of a toilet;
wherein the source directs the far-ultraviolet radiation at the number of reflective devices in order to disinfect the external surface of the toilet.

16. A method for disinfecting a lavatory, the method comprising:
determining whether a set of criteria for activation of a disinfection system to perform a disinfection process inside the lavatory has been met; and
activating the disinfection system to perform the disinfection process inside the lavatory in response to a determination that the set of criteria has been met;
wherein the disinfection system comprises a source of far ultraviolet radiation, the source located in or on a wall of the lavatory and configured to perform the disinfection process on at least one surface inside the lavatory.

17. The method of claim 16, wherein determining whether the set of criteria has been met comprises:
determining whether the lavatory is unoccupied;
determining whether the lavatory has been occupied a selected number of times since a previous disinfection of the lavatory; and
determining whether a door to the lavatory is closed.

18. The method of claim 16 further comprising:
deactivating the disinfection system to place the disinfection system in an inactive mode after completion of the disinfection process.

19. The method of claim 16 further comprising:
monitoring a door to the lavatory using a sensor system; and
deactivating the disinfection system to place the disinfection system in an inactive mode in response to a detection by the sensor system of the door to the lavatory being opened during the disinfection process.

20. The method of claim 19, wherein deactivating the disinfection system comprises:
halting emission of the far-ultraviolet radiation from an ultraviolet radiation source in less than a second after the detection by the sensor system that the door to the lavatory has opened.

21. The method of claim 16 further comprising:
reflecting the far-ultraviolet radiation onto at least one selected surface in the lavatory using at least one of a number of reflector devices located inside the lavatory or a reflective material on a plurality of surfaces inside the lavatory.

22. The method of claim 16 further comprising:
emitting the far-ultraviolet radiation from at least one ultraviolet radiation source.

23. A method for disinfecting a lavatory, the method comprising:
determining whether the lavatory is unoccupied;
determining whether the lavatory has been occupied a selected number of times since a previous disinfection of the lavatory, in response to a determination that the lavatory is unoccupied;
determining whether a door to the lavatory is closed in response to a determination that the lavatory has been occupied the selected number of times since the previous disinfection of the lavatory;
activating a disinfection system to perform a disinfection process inside the lavatory in response to a determination that the door is closed; and
deactivating the disinfection system after completion of the disinfection process;
wherein the disinfection system comprises a source of far ultraviolet radiation located in or on a ceiling or a wall of the lavatory and configured to perform the disinfection process on at least one surface inside the lavatory.

24. The apparatus of claim 23, wherein the vehicle is an aerospace vehicle selected from one of an aircraft, a spacecraft, a space shuttle, and a space station.

25. The method of claim 23 further comprising:
monitoring the door to the lavatory during the disinfection process; and
deactivating the disinfection system in response to a detection of the door to the lavatory being opened during the disinfection process.

26. The method of claim 23 further comprising:
maintaining the disinfection system in an inactive mode in response to a determination that the lavatory is unoccupied or a determination that the door to the lavatory is not closed.

* * * * *

UNITED STATES PATENT AND TRADEMARK OFFICE
CERTIFICATE OF CORRECTION

PATENT NO. : 9,623,133 B2
APPLICATION NO. : 14/610022
DATED : April 18, 2017
INVENTOR(S) : James J. Childress, Mark L. Cloud and Karen Lee Hills It is certified that error appears in the above-identified patent and that said Letters Patent is hereby corrected as shown below:

In the Claims

Column 15, Lines 27-28, change "far ultraviolet" to --far-ultraviolet--
Column 16, Lines 31-32, change "far ultraviolet" to --far-ultraviolet--

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*